United States Patent
Bulbrook (10) Patent No.: US 8,171,930 B2
(45) Date of Patent: May 8, 2012

(54) POWDER INHALER FEATURING REDUCED COMPACTION INHALER

(75) Inventor: George Lee Bulbrook, Dereham (GB)

(73) Assignee: 135540 Ontario Inc., Concord, Ontario (CA)

( * ) Notice: Subject to any disclaimer, the term of this patent is extended or adjusted under 35 U.S.C. 154(b) by 1121 days.

(21) Appl. No.: 11/572,382

(22) PCT Filed: Jul. 12, 2005

(86) PCT No.: PCT/CA2005/001080
§ 371 (c)(1),
(2), (4) Date: Jan. 21, 2008

(87) PCT Pub. No.: WO2006/010248
PCT Pub. Date: Feb. 2, 2006

(65) Prior Publication Data
US 2008/0142006 A1    Jun. 19, 2008

Related U.S. Application Data

(60) Provisional application No. 60/590,912, filed on Jul. 26, 2004.

(51) Int. Cl.
*A61M 15/00* (2006.01)
*A61M 13/00* (2006.01)
*B65D 83/06* (2006.01)

(52) U.S. Cl. ......... 128/203.15; 128/203.12; 128/203.23; 604/58

(58) Field of Classification Search ............. 128/203.12, 128/203.15, 203.21, 203.23; 604/58
See application file for complete search history.

(56) References Cited

U.S. PATENT DOCUMENTS

| | | | |
|---|---|---|---|
| 2,517,482 A | 8/1950 | Hall | |
| 5,694,920 A * | 12/1997 | Abrams et al. | 128/200.16 |
| 5,699,789 A | 12/1997 | Hendricks | |
| 5,924,417 A * | 7/1999 | Braithwaite | 128/203.15 |

(Continued)

FOREIGN PATENT DOCUMENTS

CA     2091060     4/1992

(Continued)

OTHER PUBLICATIONS

Supplementary Search Report received on the corresponding European Patent Application No. 05763550.0, dated Dec. 16, 2010.

(Continued)

*Primary Examiner* — Justine Yu
*Assistant Examiner* — Valerie L Skorupa
(74) *Attorney, Agent, or Firm* — Bereskin & Parr LLP/ S.E.N.C.R.L., s.r.l.; Philip C. Mendes da Costa (57) ABSTRACT

An inhaler has an air inlet port and an entry passage extending from the air inlet port to a contact chamber inlet port, a contact chamber and an inhaler air outlet port. The contact chamber has first and second opposed ends, a sidewall extending between the first and second opposed ends that in cross section is curved, the second opposed end having an opening in air flow communication with a dosage chamber and a contact chamber outlet port. The contact chamber inlet port is provided in the sidewall and faces a portion of the sidewall opposed to contact chamber inlet port. The contact chamber has a cross sectional area that is greater than the cross sectional area of the entry passage.

32 Claims, 4 Drawing Sheets

U.S. PATENT DOCUMENTS

| | | | |
|---|---|---|---|
| 6,070,575 A * | 6/2000 | Gonda et al. | 128/203.12 |
| 6,116,239 A * | 9/2000 | Volgyesi | 128/203.15 |
| 2002/0033177 A1* | 3/2002 | Ohki et al. | 128/203.15 |
| 2003/0000523 A1* | 1/2003 | Citterio | 128/203.15 |
| 2003/0188747 A1* | 10/2003 | Ohki et al. | 128/203.15 |
| 2005/0056275 A1* | 3/2005 | Ingle et al. | 128/200.23 |

FOREIGN PATENT DOCUMENTS

| | | |
|---|---|---|
| CA | 2122026 | 5/1993 |
| CA | 2339973 | 2/2000 |
| EP | 1106196 A2 | 6/2001 |
| JP | 9322938 A | 12/1997 |
| JP | 2001161788 | 6/2001 |
| JP | 2007522881 | 8/2008 |
| WO | 9609085 | 3/1996 |
| WO | 99/07426 A1 | 2/1999 |
| WO | 2006010248 | 2/2006 |

OTHER PUBLICATIONS

English translation of the abstract of the Japanese patent publication No. 9322938, published on Dec. 16, 1997.

European Supplementary Search Report corresponding to application No. 05763550.0 dated Jan. 4, 2011.

Japanese Office Action corresponding to application No. 2007-522881 dated Aug. 31, 2010.

Japanese Office Action corresponding to application No. 2007-522881 dated Aug. 23, 2011.

International Search Report corresponding to international application No. PCT/CA2005/001080 dated Nov. 9, 2005.

* cited by examiner

FIG. 3

POWDER INHALER FEATURING REDUCED COMPACTION INHALER

FIELD OF THE INVENTION

This invention relates to hand held inhalers for delivering a powdered medicament to a user.

BACKGROUND OF THE INVENTION

Various different designs of hand held inhalers for delivering powdered medicaments to a patient have been developed. In many applications, it important to be able to reliably and repeatedly delivers a particular dosage of a medicament to a user. Powdered medicaments tend to agglomerate and form aggregated particles that are too large to remain entrained in an airflow stream that travels into the lungs of a user. Aggregated particles (e.g. those larger than about 5 microns) tend to impact on the throat of a user as opposed to passing through the airways to the lungs of a user. Thus, a full dosage may not be received in the lungs of a user. Accordingly, inhalers have utilized different mechanisms to de-aggregate the medicament. These mechanisms include using a pressurized propellant to assist in disbursing the medicament, the use of impellers to produce turbulence to which the aggregated particles are exposed and the configuration of the inhaler to produce a turbulent flow of air to de-aggregate the powdered medicament.

Inhalers that do not use a pressurized propellant typically use a stream of air traveling through the inhaler to remove the medicament from a storage chamber. A problem with some of these designs is that the stream of air is directed at the storage chamber at an angle that tends to compact the medicament thereby increasing the likelihood that aggregated particles that are too large to remain entrained in an airflow stream that travels into the lungs of a user will be formed.

SUMMARY OF THE INVENTION

In accordance to the instant invention, an inhaler is provided with an entrance passage that is positioned upstream of a contact chamber. The contact chamber is in fluid for communication with a storage chamber that contains a particulate material that is to be inhaled. The entrance passage is configured such that, as of a position immediately upstream of the contact chamber, the flow of air in the entrance passage is generally linear. This flow of air may have laminar and turbulent flow components. As the flow of air upstream of the contact chamber is generally linear, the air that enters the contact chamber has a forward velocity component. The forward velocity component is sufficient such that the air impacts on the wall of the contact chamber opposite to the air inlet to the contact chamber and essentially replaces the boundary layer of air that is adjacent the wall of the contact chamber. The incoming air travels along the wall of the contact chamber to the end of the contact chamber in which the storage chamber is positioned. At this position, the air changes direction and a turbulent flow of air is produced that travels over the particulate material in the storage chamber. Due to the turbulence, some of the air is drawn down into the storage chamber and removes the particulate material from the storage chamber with a reduced amount of compaction of the medicament compared to the compaction that occurs when a jet of air is directed directly into the storage chamber. Accordingly, this permits the inhaler to deliver a generally de-aggregated particulate material to the mouth of a user.

The storage chamber may contain multiple doses of a particulate material. Preferably, the storage chamber contains a single dosage of the particulate material.

Downstream of the contact chamber, the inhaler may have an exit passageway that is configured to break up aggregated powdered medicament that may be in the air stream that exits the contact chamber. For example, the exit passageway may be configured to produce a turbulent airflow or a cyclonic airflow that will utilize shear forces in the airflow itself to break up aggregated particulate matter. In addition, or alternately, the exit passageway may be configured to produce a sudden change in the direction of flow of the medicament so that the medicament impacts against a wall of the exit passageway as the air flow passes through the inhaler to thereby assist in the de-aggregation of the aggregated powdered medicament.

Accordingly, in accordance with the first embodiment of the instant invention there is provided an inhaler comprising:

(a) an air inlet port;

(b) an entry passage extending from the air inlet port to a contact chamber inlet port;

(c) a contact chamber having first and second opposed ends, a sidewall extending between the first and second opposed ends that in cross section is curved, the second opposed end having an opening in air flow communication with a dosage chamber and a contact chamber outlet port, the contact chamber inlet port provided in the sidewall and facing a portion of the sidewall opposed to contact chamber inlet port, the contact chamber having a cross sectional area that is greater than the cross sectional area of the entry passage; and, (d) an inhaler air outlet port positioned downstream of the contact chamber.

In one embodiment, the contact chamber outlet port is positioned in the sidewall intermediate the contact chamber inlet port and the second opposed end.

In another embodiment, the contact chamber inlet port is positioned adjacent the first opposed end.

In another embodiment, the entry passage has a width and a length and the length is 3 or more times the width.

In another embodiment, the length is 5-10 times the width.

In another embodiment, the entry passage has a longitudinally extending axis and the contact chamber has a longitudinally extending axis that is approximately perpendicular to the axis of the entry passage.

In another embodiment, the entry passage has at least one sidewall and at the contact chamber inlet port, the at least one sidewall of the entry passage meets the sidewall of the contact chamber at about a right angle.

In another embodiment, the inhaler further comprises an exit passage positioned between the contact chamber and the inhaler air outlet port, the exit passage is configured to induce aggregated particles to break up into smaller components that are suitable for inhalation.

In another embodiment, the inhaler further comprises an exit passage having a flow path, the exit passage is positioned between the contact chamber and the inhaler air outlet port, and the exit passage includes an impact surface positioned in the flow path through the exit passage.

In another embodiment, the inhaler further comprises an exit passage positioned between the contact chamber and the inhaler air outlet port, the exit passage comprises a first passage having a first end in air flow communication with the contact chamber outlet port, an opposed second end, at least one sidewall extending between the first and second ends and a first passage outlet port provided in the at least one sidewall adjacent the second end.

In another embodiment, the inhaler further comprises a swirl chamber positioned between the contact chamber and the inhaler air outlet port.

In another embodiment, the inhaler further comprises a member having a plurality of dosage chambers, the member being movable mounted in the inhaler whereby each dosage chamber is selectively positionable in airflow communication with the opening in the second end of the contact chamber.

In another embodiment, each dosage chamber has on open end that is selectively positionable in airflow communication with the opening in the second end of the contact chamber. Preferably, at least some of the dosage chambers have differing levels of particulate matter.

In another embodiment, the particulate matter may be any medicament and, preferably, the particulate matter comprises or is derived from methacholine.

In accordance with another aspect of the present invention, there is provided an inhaler comprising:

(a) an air inlet port;

(b) an entry passage extending from the air inlet port to a contact chamber inlet port;

(c) a contact chamber having first and second opposed ends, a sidewall extending between the first and second opposed ends that in cross section is curved, and a contact chamber outlet port, the contact chamber inlet port provided in the sidewall, the length of the entry passage and the orientation of the contact chamber inlet port selected such that, upon inhalation, a jet of air is directed from the entry passage to the sidewall to displace a boundary layer of air on the sidewall and cause the air to travel adjacent the sidewall to an opening in the second opposed end, the contact chamber having a cross sectional area that is greater than the cross sectional area of the entry passage; and, (d) an inhaler air outlet port positioned downstream of the contact chamber.

In one embodiment, the contact chamber outlet port is positioned in the sidewall intermediate the contact chamber inlet port and the second opposed end.

In another embodiment the contact chamber inlet port is positioned adjacent the first opposed end.

In another embodiment, the entry passage has a width and a length and the length is 3 or more times the width and, preferably, the length is 5-10 times the width.

In another embodiment, the entry passage has a longitudinally extending axis and the contact chamber has a longitudinally extending axis that is approximately perpendicular to the axis of the entry passage.

In another embodiment, the entry passage has at least one sidewall and at the contact chamber inlet port, the at least one sidewall of the entry passage meets the sidewall of the contact chamber at about a right angle.

In another embodiment, the inhaler further comprises an exit passage positioned between the contact chamber and the inhaler air outlet port, the exit passage is configured to induce aggregated particles to break up into smaller components that are suitable for inhalation.

In another embodiment, the inhaler further comprises an exit passage having a flow path, the exit passage is positioned between the contact chamber and the inhaler air outlet port, and the exit passage includes an impact surface positioned in the flow path through the exit passage.

In another embodiment, the inhaler further comprises an exit passage positioned between the contact chamber and the inhaler air outlet port, the exit passage comprises a first passage having a first end in air flow communication with the contact chamber outlet port, an opposed second end, at least one sidewall extending between the first and second ends and a first passage outlet port provided in the at least one sidewall adjacent the second end.

In another embodiment, the inhaler further comprises a swirl chamber positioned between the contact chamber and the inhaler air outlet port.

In another embodiment, the inhaler further comprises a member having a plurality of dosage chambers, the member being movable mounted in the inhaler whereby each dosage chamber is selectively positionable in airflow communication with the opening in the second end of the contact chamber.

In another embodiment, each dosage chamber has on open end that is selectively positionable in airflow communication with the opening in the second end of the contact chamber.

In another embodiment at least some of the dosage chambers have differing levels of particulate matter.

In another embodiment, the particulate matter comprises or is derived from methacholine.

In accordance with another embodiment of the present invention, there is provided a method comprising:

(a) producing a flow of air that enters into an entry passage to develop a generally linear flow of air;

(b) causing the air to enter into a contact chamber having a sidewall to displace a boundary layer of air on the sidewall and cause the air to travel through an annular portion of the contact chamber that is adjacent the sidewall to a dosage chamber positioned adjacent one end of the contact chamber and remove particulate material in the dosage chamber;

(c) causing the air to travel though a central portion of the contact chamber that is interior to the annular portion of the contact chamber to a contact chamber air exit port; and, (d) causing the air to subsequently travel to an inhaler outlet port.

In one embodiment, the contact chamber has an inlet port and a sidewall and the contact chamber inlet port and the sidewall are configured such that air entering the contact chamber travels towards the dosage chamber utilizing the Coanda effect.

In another embodiment, the method further comprises causing aggregated particulate material in the air downstream of the dosage chamber to de-aggregate.

In another embodiment, the method further comprises utilizing airflow downstream of the dosage chamber to de-aggregate aggregated particulate material.

In another embodiment, the method further comprises selecting a dosage of medicament for the dosage chamber.

One advantage of the instant design is that the airflow in the contact chamber is designed to scour the medicament from a dosage or storage chamber. In the prior art, inhalers have been developed wherein an air inlet is configured to produce a jet of air which is aimed directly at the medicament. The incoming jet of air will disburse the medicament. However, the force of the incoming air has a tendency to aggregate a portion of the powdered medicament. In contrast, in accordance with the instant invention, the airflow produced in the contact chamber is designed to remove medicament from the dosage chamber without significantly compacting the medicament. The configuration of the inhaler creates a turbulent environment around the dosage chamber. The shear forces in the airflow in the vicinity of the dosage chamber results in the powdered medicament being removed or lifted from the dosage chamber without any significant compacting force being applied to the medicament. This reduces the amount of aggregated powdered medicament that is entrained in the air stream.

BRIEF DESCRIPTION OF THE DRAWINGS

These and other advantages of the instant invention will be more clearly explained in accordance with the following description of a preferred embodiment of the invention in which.

DETAILED DESCRIPTION OF THE INVENTION

As shown in the Figures, inhaler 10 comprises a top cover 12, a first intermediate member 14, a second intermediate member 16, a movable member 18 that contains a plurality of dosage chambers 22 and a bottom cover 20. These parts define an airflow passage through the inhaler that comprises an air inlet port 24 for the inhaler 10, an entrance passage 26 (see FIG. 4), a contact chamber 28 (see FIG. 3) and an exit passage 30 that is upstream from air exit port 32. It will be appreciated that inhaler 10 may be constructed from any series of parts which will produce the airflow path described herein.

Upon entering the inhaler through inlet port 24, the air travels through entrance passage 26 from inlet port 24 to outlet port 36 of passage 26. Entrance passage 26 has a length "L" and a width "W". The relative length of the passage 26 (i.e. the ratio of the length L to the width W of the passage 26 is sufficiently long to establish a generally linear flow of air. Preferably, the length L of entrance passage 26 is three or more times the width W of entrance passage 26, more preferably, the length is 5 or more times the width W and, most preferably, the length L is to 10 times the width W. Accordingly, at outlet port 36 the air traveling through inhaler 10 is essentially linear. Further, the air will have a pressure that is higher than the pressure in contact chamber 28.

Figure 2:
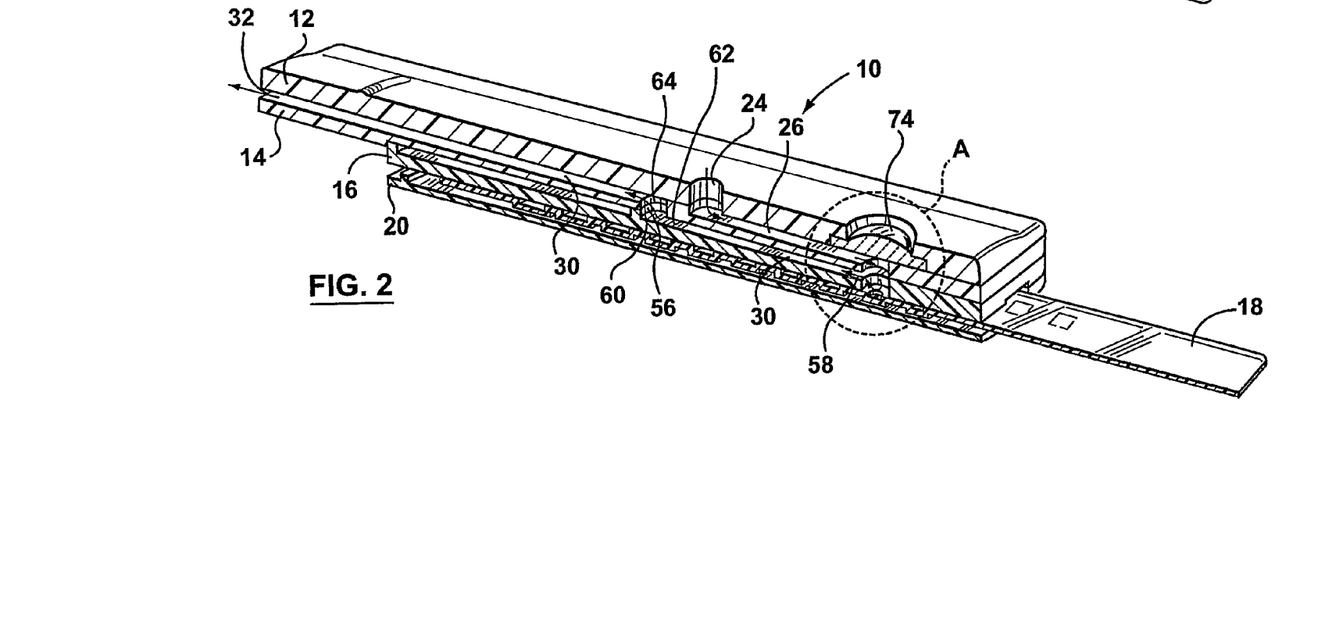
FIG. 2 is a cross section along the line 2-2 in FIG. 1.

Entrance passage 26 need not extend in a straight line. Further, the cross-sectional shape of entrance passage 26 may be of any particular configuration. For example, it may be rectangular as shown in FIG. 2. Alternately, it could be square, oval, cylindrical or the like. Preferably, entrance passage 26 has a non-circular cross section so as to inhibit cyclonic flow.

Figure 1:
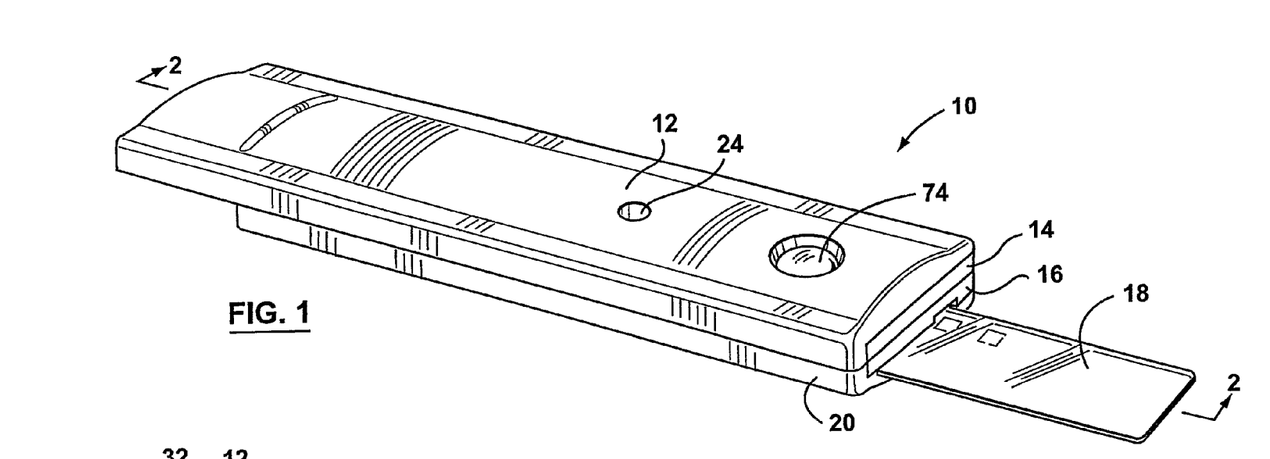
FIG. 1 is a perspective view of an inhaler according to the present invention.

As shown in FIG. 1, upon entering inhaler 10 via inlet port 24, the incoming air bends 90° to travel longitudinally through entrance passage 26. It will be appreciated that inlet port 24 may be oriented in the same direction as entrance passage 26 such that the air may travel linearly through inlet 24 and entrance passage 26.

Figure 3:
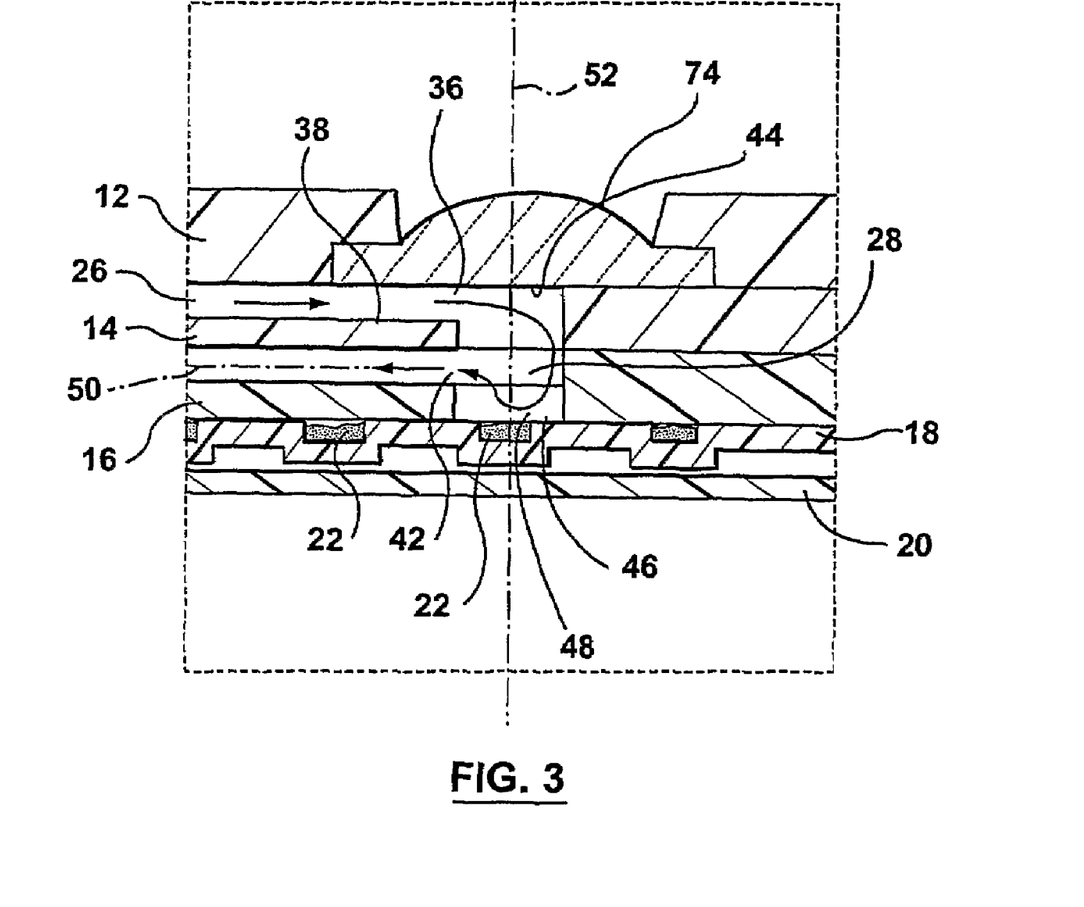
FIG. 3 is an enlarged perspective view of area A shown in FIG. 2.
Figure 4:
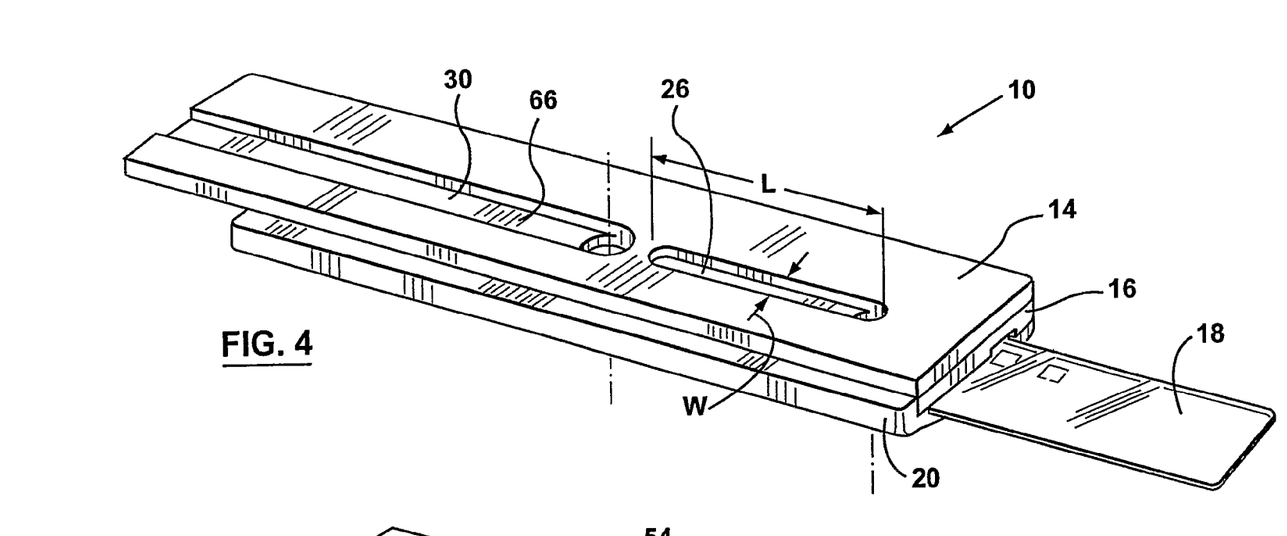
FIG. 4 is a perspective view of the inhaler of FIG. 1 with the top cover removed so as to show the air inlet passageway and an air exit passageway.
Figure 5:
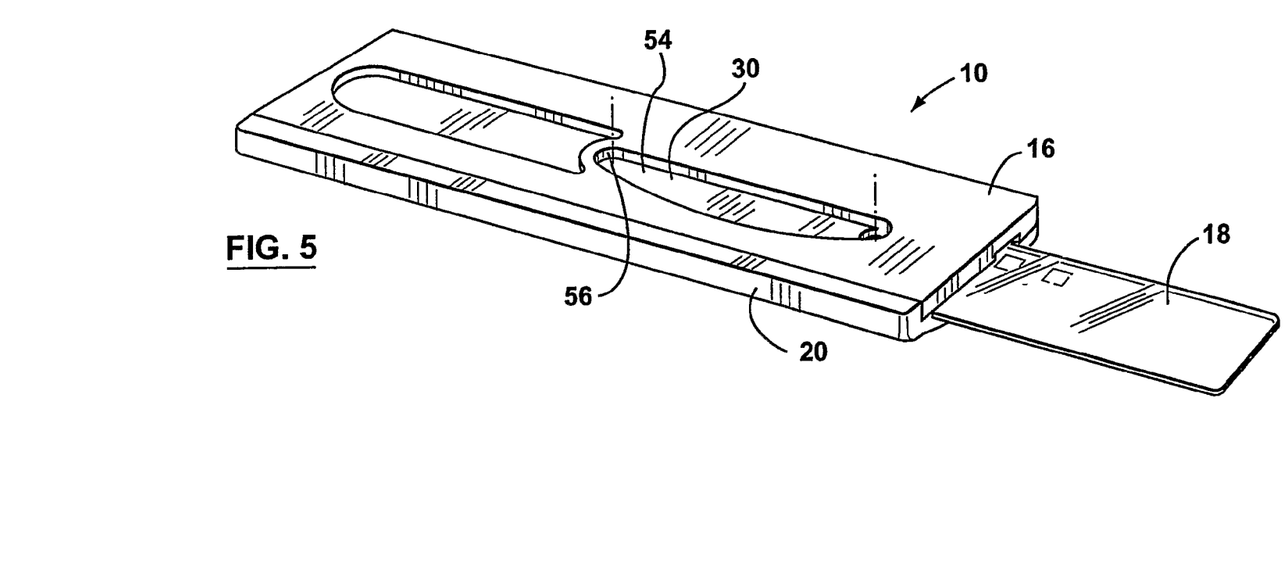
FIG. 5 is a perspective view of the inhaler of FIG. 1 with an intermediate member removed so as to show a swirl chamber.

Contact chamber 28 is positioned downstream from entrance passage 26. As shown in FIG. 3, contact chamber 28 has first and second opposed ends 44 and 46 and a sidewall 48 extending therebetween. The second opposed end 46 has an opening therein such that contact chamber 28 may be in airflow communication with a dosage chamber 22. As shown in FIG. 3, second opposed end 46 does not have any wall portions and, accordingly, the second opposed end of the contact chamber comprises an open end. Alternately, it will be appreciated that second opposed end 46 may have a wall portion provided the wall portion has an opening which is at least about the size of the opening into dosage chamber 22.

Contact chamber 28 has a larger cross-sectional area than entrance passage 26 and, accordingly, will have a static pressure that is lower than the static pressure of the entrance passage 26. Accordingly, the air entering contact chamber 28 through outlet port 36 will produce a jet of air directly against sidewall 48 of contact chamber 28. This incoming jet of air will displace the existing boundary layer of air on sidewall 48 and, as it moves along sidewall 48, will remove particulate matter thereon thereby effectively cleaning sidewall 48.

Sidewall 38 of passage 26 and sidewall 48 of contact chamber 28 are configured such that the Coanda effect produces airflow in contact chamber 28 that travels towards dosage chamber 22. As shown in FIG. 3, sidewall 38 of the entrance passage 26 meets the sidewall 48 of contact chamber 28 preferably at about a right angle. It will be appreciated by those skilled in the art that sidewalls 38 and 48 do not have to meet exactly at a right angle in order for the Coanda effect to produce airflow in contact chamber 28. The greater the angle, or if the corner where sidewalls 38 and 48 meet are radiused, then the more the Coanda effect will be dispersed. However, it will be appreciated that the maximal airflow need not be produced provided that the airflow that is set up by the Coanda effect is sufficient to remove the medicament from the dosage chamber 22.

In accordance with the instant invention, outlet port 36 is oriented so that the air entering contact chamber 28 is not directed towards dosage chamber 22. Instead, outlet port 36 directs the air entering contact chamber 28 to a portion of the sidewall 48 of contact chamber 28. Preferably, the portion of the sidewall 48 that is contacted by the incoming air is immediately opposite outlet port 36. For example, the longitudinal axis 50 of entrance passage 26 is preferably essentially perpendicular to the axis 52 of contact chamber 28. Accordingly, the incoming air is not provided with a tangential component and, therefore, the formation of a cyclonic flow of air in contact chamber is not encouraged.

In a cross section perpendicular to axis 52, sidewall 48 is curved. As shown in FIG. 2, contact chamber 48 is cylindrical and, accordingly, in cross section, sidewall 48 is circular. It will be appreciated that in cross section, sidewall 48 may have any smooth cross-section (i.e. no corners). Accordingly, sidewall 48 may be oval in cross section.

Also, as shown in FIG. 3, outlet port 36 is positioned adjacent first opposed end 44 of contact chamber 28. It will be appreciated that outlet port 36 need not be positioned immediately adjacent first opposed end 44 and may in fact be spaced therefrom.

As shown in FIG. 3, outlet port 42 may be positioned on sidewall 48 intermediate outlet port 36 and second opposed end 46. Accordingly, after the incoming air has traveled from outlet port 36 to second opposed end 46, the air reverses direction and passes upwardly through a central portion of contact chamber 28 and then laterally through the boundary layer adjacent side wall 48 to outlet port 42.

It will be appreciated that outlet port 42 may be positioned in first end 44. If outlet port 42 is provided intermediate outlet port 36 and second opposed end 46, then the air traveling between the outlet port 36 and the dosage chamber 22 will travel over outlet port 42. Accordingly, some of the incoming air will pass into exit passage 30 prior to contacting dosage chamber 22. Preferably, the construction of outlet port 42 is the same as the construction of outlet port 36, namely the sidewall of exist passage 30 meets sidewall 48 of contact chamber 28 at about a right angle. This results in a reduced amount of air by passing dosage chamber 22. The greater the variance from 90° of the angle where sidewall 48 meets the side wall of exit passage, or if the side walls are radiused so as to form a curved connecting portion, then the amount of air which bypasses dosage chamber 22 will be increased.

At second end 46, the air traveling along sidewall 48 encounters the top surface of moveable member 18. The edge forms a discontinuity in the flow path of the air. Due to the discontinuity, the air is redirected to flow inwardly towards the centre of contact chamber 28 and this redirection results in a turbulent flow of air. As the air travels over dosage chamber 22, some of the air will travel downwardly into dosage chamber 22 and will entrain the particulate material therein. It will be appreciated that dosage chamber 22 may have a diameter that is the same as or smaller than the diameter of contact chamber 28. It will also be appreciated that contact chamber 28 may have an end wall that has an opening therein with which dosage chamber 22 may be aligned. Accordingly, the redirection of the air stream may be produced by the air encountering an end wall of contact chamber 28, the upper surface of moveable member 18 or the particulate material in dosage chamber 22.

In one embodiment, the air may travel directly from outlet port 42 to inhaler air exit port 32. Preferably, an exit passage 30 is positioned downstream of contact chamber 28 and upstream of inhaler air exit port 32. Exit passage 30 is configured to induce aggregated particles that are in the air stream to break up into smaller components that are suitable for inhalation. For example, exit passage 30 may be configured to produce turbulent flow therethrough such as by adding ridges or abruptions to the surface geometry. Alternately, exit passage may be configured to produce a swirling or cyclonic flow (e.g. by passage 30 being asymmetrical) whereby the air flow produces eddies which are strong enough to de-aggregate slugs of particulate matter which may be in the air stream. Accordingly, exit passage 30 may incorporate a swirl chamber 54 or the like.

Alternately, exit passage 30 may incorporate an impact surface 56. Impact surface 56 is positioned in the airflow stream such that particles that are entrained in the airflow stream will contact impact surface 56 as the air travels through exit passage 30. It will be appreciated that exit passage may contain a plurality of impact surfaces 56. For example, as shown in FIG. 2, air traveling from outlet port 42 will travel through a first passage (which may be swirl chamber 54) from first end 58 to second end 60. Impact surface 56 is located adjacent second end 60. At least one sidewall 62 extends between first and second ends 58 and 60 and is provided with first passage outlet port 64 that is preferably positioned adjacent second end 60. Air with entrained medicament will travel through first passage 54 until a position adjacent first passage outlet port 64. At that position, the air will change direction. Some or all of the slugs of aggregated medicament in the air stream may have too much momentum to travel directly through outlet port 64. Instead, due to their momentum, the slugs may continue on and contact impact surface 56 resulting in a break up of the powder slugs. The de-aggregated medicament may then be re-entrained in the air stream passing through outlet port 64. Outlet port 64 may be directly connected to outlet port 32 of inhaler 10. Alternately, exit passage 30 may comprise a second passage 66 that extends from first passage outlet port 64 to inhaler outlet port 32.

Figures 6, 6A:
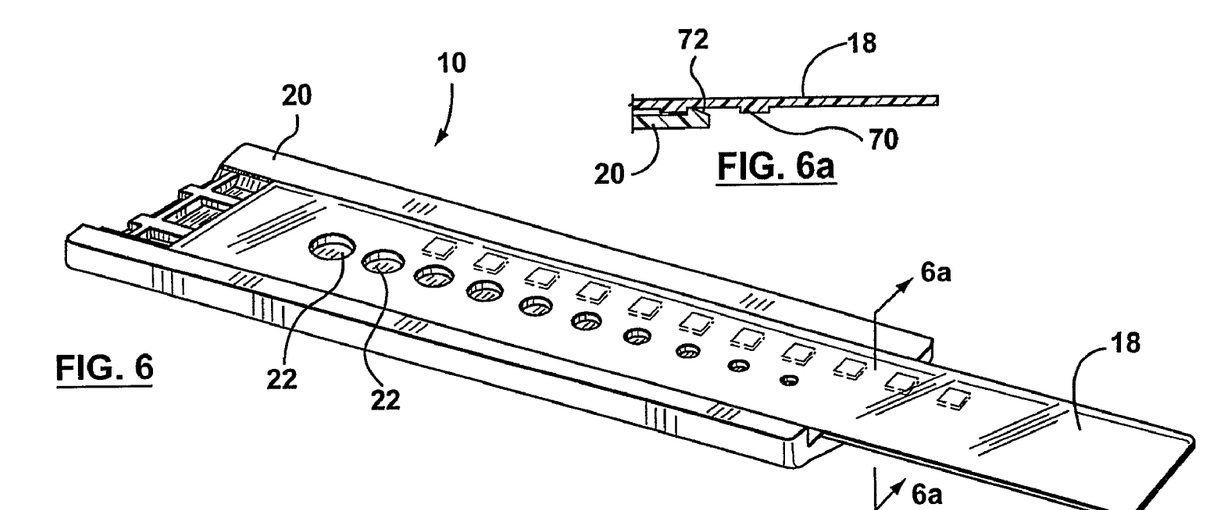
FIG. 6 is a perspective view of the inhaler of FIG. 1 with a further intermediate panel removed so as to show a member containing a plurality of dosage chambers.
FIG. 6a is a cross section along the line 6a-6a in FIG. 6.
Figure 7:
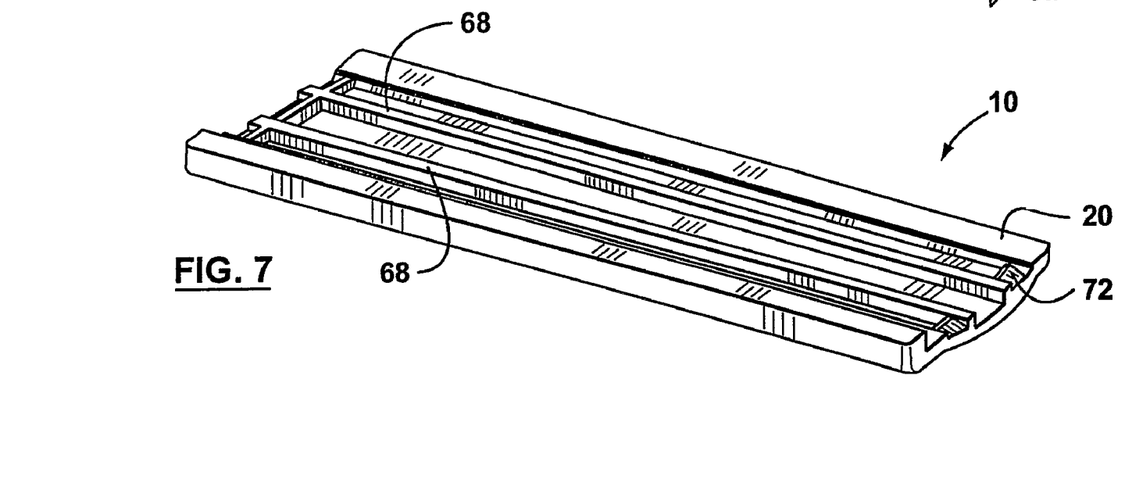
FIG. 7 is a perspective view of the inhaler of FIG. 1 with the member containing the dosage chambers removed.

The medicament may be provided in one or more dosage chambers 22 which are provided in movable member 18. As shown in FIG. 6, all of the dosage chambers need not be the same size. In particular, the dosage chambers 22 may vary in size and, preferably, the chambers are set out in a series with each subsequent chamber being larger than the preceding chamber. Accordingly, each chamber 22 may contain a different amount of medicament. As shown in FIG. 7, movable member 18 is slidably mounted on rails 68 of bottom cover 20 and may merely be seated on rails 68. However, in an alternate embodiment, it will be appreciated that movable member 18 may be mounted for linear movement in inhaler 10 by any other means known in the art. Alternately, movable member 18 may be constructed to move in a different direction. For example, movable member 18 may be generally circular and may be rotatably mounted in inhaler 10.

Preferably, as shown in FIG. 6, each dosage chamber 22 has an open top. Accordingly, when dosage chamber 22 is aligned with second opposed end 46 of contact chamber 28, contact chamber 28 is in airflow communication with a dosage chamber 22. Accordingly, it is not necessary to break a seal that closes dosage chamber 22. Instead, the lower surface of second intermediate member 16 may function as a closure of dosage chambers 22.

As shown in FIG. 6a, movable member 18 may be provided with a plurality of detent members 70 which are adapted to engage end wall 72 of bottom cover 20. Each detent member 70 is positioned such that when the detent member encounters end wall 72, a particular dosage chambers is aligned with contact chamber 28. Slidable member 18 may be provided with dosage markings thereon so as to indicate to a user the dosage that is aligned with contact chamber 28 when a particular detent member engages end wall 72. It will also be appreciated by those skilled in the art that other first and second engagement members may be utilized to position dosage chambers 22 in alignment with contact chamber 28.

Optionally, as shown in FIG. 1, inhaler 10 may be provided with a viewing window 74 adjacent first opposed end 44 of contact chamber 28. Accordingly, a user may use viewing window 74 to confirm that a dosage chamber is aligned with contact chamber 28 and, in addition, to determine whether all of the medicament was withdrawn from dosage chamber 22.

In operation, a user may move slidable member 18 so as to position a dosage chamber 22 containing a desired amount of medicament in alignment with contact chamber 28. The user may then inhale through inhaler outlet port 32. Upon inhalation, the user will cause air to enter inhaler 10 via inlet port 24 and to travel through entrance passage 26 at which time the airflow will be converted to a generally linear airflow. This linear airflow will enter contact chamber 28 via outlet port 36 of passage 26 as a jet. Some of the air will contact the sidewall 48 opposite outlet port 36. The incoming air will displace the layer of air on sidewall 48 and will travel along sidewall 48 towards second opposed end 46. The incoming air will remove the medicament from dosage chamber 22. The air will then travel in the opposite direction through the central portion of contact chamber 28 (interior to the annular boundary layer surrounding sidewall 48). The return air will then exit contact chamber 36 through outlet port 42. If the inhaler includes an exit passage 30, the air will then travel through exit passage 30 to inhaler air exit port 32.

It will be appreciated by those skilled in the art that various modifications and additions may be made to the inhaler and all of these modifications and additions are within the scope of the following claims.

The invention claimed is:

1. An inhaler comprising:

(a) an air inlet port;

(b) an entry passage extending from the air inlet port to a contact chamber inlet port;

(c) a contact chamber having first and second opposed ends, a sidewall extending between the first and second opposed ends that in cross section is curved, the second opposed end having an opening in air flow communication with a dosage chamber and a contact chamber outlet port positioned in the sidewall intermediate every contact chamber inlet port and the second opposed end, the contact chamber inlet port provided in the sidewall and facing a portion of the sidewall opposed to contact chamber inlet port, the contact chamber having a cross sectional area that is greater than the cross sectional area of the entry passage; and, (d) an inhaler air outlet port positioned downstream of the contact chamber.

2. The inhaler of claim 1 wherein the contact chamber inlet port is positioned adjacent the first opposed end.

3. The inhaler of claim 1 wherein the entry passage has a width and a length and the length is 3 or more times the width.

4. The inhaler of claim 3 wherein the length is 5-10 times the width.

5. The inhaler of claim 1 wherein the entry passage has a longitudinally extending axis and the contact chamber has a longitudinally extending axis that is approximately perpendicular to the axis of the entry passage.

6. The inhaler of claim 1 wherein the entry passage has at least one sidewall and at the contact chamber inlet port, the at least one sidewall of the entry passage meets the sidewall of the contact chamber at about a right angle.

7. The inhaler as claimed in claim 1 further comprising an exit passage positioned between the contact chamber and the inhaler air outlet port, the exit passage is configured to induce aggregated particles to break up into smaller components that are suitable for inhalation.

8. The inhaler of claim 1 further comprising an exit passage having a flow path, the exit passage is positioned between the contact chamber and the inhaler air outlet port, the exit passage includes an impact surface positioned in the flow path through the exit passage.

9. The inhaler of claim 1 further comprising an exit passage positioned between the contact chamber and the inhaler air outlet port, the exit passage comprises a first passage having a first end in air flow communication with the contact chamber outlet port, an opposed second end, at least one sidewall extending between the first and second ends and a first passage outlet port provided in the at least one sidewall adjacent the second end.

10. The inhaler of claim 1 further comprising a swirl chamber positioned between the contact chamber and the inhaler air outlet port.

11. The inhaler of claim 1 further comprising a member having a plurality of dosage chambers, the member being movable mounted in the inhaler whereby each dosage chamber is selectively positionable in air flow communication with the opening in the second end of the contact chamber.

12. The inhaler of claim 11 wherein each dosage chamber has an open end which is selectively positionable in air flow communication with the opening in the second end of the contact chamber.

13. The inhaler of claim 12 wherein at least some of the dosage chambers have differing levels of particulate matter.

14. The inhaler of claim 13 wherein the particulate matter comprises or is derived from methacholine.

15. An inhaler comprising:

(a) an air inlet port;

(b) an entry passage extending from the air inlet port to a contact chamber inlet port;

(c) a contact chamber having first and second opposed ends, a sidewall extending between the first and second opposed ends that in cross section is curved, and a contact chamber outlet port positioned in the sidewall intermediate every contact chamber inlet port and the second opposed end, the contact chamber inlet port provided in the sidewall, the length of the entry passage and the orientation of the contact chamber inlet port selected such that, upon inhalation, a jet of air is directed from the entry passage to the sidewall to displace a boundary layer of air on the sidewall and cause the air to travel adjacent the sidewall to an opening of a dosage chamber in the second opposed end, the contact chamber having a cross sectional area that is greater than the cross sectional area of the entry passage; and, (d) an inhaler air outlet port positioned downstream of the contact chamber.

16. The inhaler of claim 15 wherein the contact chamber inlet port is positioned adjacent the first opposed end.

17. The inhaler of claim 15 wherein the entry passage has a width and a length and the length is 3 or more times the width.

18. The inhaler of claim 17 wherein the length is 5-10 times the width.

19. The inhaler of claim 15 wherein the entry passage has a longitudinally extending axis and the contact chamber has a longitudinally extending axis that is approximately perpendicular to the axis of the entry passage.

20. The inhaler of claim 15 wherein the entry passage has at least one sidewall and at the contact chamber inlet port, the at least one sidewall of the entry passage meets the sidewall of the contact chamber at about a right angle.

21. The inhaler as claimed in claim 15 further comprising an exit passage positioned between the contact chamber and the inhaler air outlet port, the exit passage is configured to induce aggregated particles to break up into smaller components that are suitable for inhalation.

22. The inhaler of claim 15 further comprising an exit passage having a flow path, the exit passage is positioned between the contact chamber and the inhaler air outlet port, the exit passage includes an impact surface positioned in the flow path through the exit passage.

23. The inhaler of claim 15 further comprising an exit passage positioned between the contact chamber and the inhaler air outlet port, the exit passage comprises a first passage having a first end in air flow communication with the contact chamber outlet port, an opposed second end, at least one sidewall extending between the first and second ends and a first passage outlet port provided in the at least one sidewall adjacent the second end.

24. The inhaler of claim 15 further comprising a swirl chamber positioned between the contact chamber and the inhaler air outlet port.

25. The inhaler of claim 15 further comprising a member having a plurality of dosage chambers, the member being movable mounted in the inhaler whereby each dosage chamber is selectively positionable in air flow communication with the opening in the second end of the contact chamber.

26. The inhaler of claim 25 wherein each dosage chamber has an open end which is selectively positionable in air flow communication with the opening in the second end of the contact chamber.

27. The inhaler of claim 26 wherein at least some of the dosage chambers have differing levels of particulate matter.

28. The inhaler of claim 27 wherein the particulate matter comprises or is derived from methacholine.

29. A method comprising:
   (a) producing a flow of air that enters into an entry passage to develop a generally linear flow of air;
   (b) causing the air to enter into a contact chamber having first and second opposed ends, a sidewall extending between the first and second opposed ends that in cross section is curved, the second opposed end having an opening in air flow communication with a dosage chamber, and a contact chamber outlet port positioned in the sidewall intermediate every contact chamber inlet port and the second opposed end to displace a boundary layer of air on the sidewall and cause the air to travel through an annular portion of the contact chamber that is adjacent the sidewall to the dosage chamber positioned adjacent one end of the contact chamber utilizing the Coanda effect and remove particulate material in the dosage chamber;
   (c) causing the air to travel though a central portion of the contact chamber that is interior to the annular portion of the contact chamber to the contact chamber air outlet port; and,
   (d) causing the air to subsequently travel to an inhaler outlet port.

30. The method of claim 29 further comprising causing aggregated particulate material in the air downstream of the dosage chamber to de-aggregate.

31. The method of claim 29 further comprising utilizing airflow downstream of the dosage chamber to de-aggregate aggregated particulate material.

32. The method of claim 29 further comprising selecting a dosage of medicament for the dosage chamber.

* * * * *